United States Patent [19]

Glamkowski et al.

[11] Patent Number: 5,536,717
[45] Date of Patent: Jul. 16, 1996

[54] 7-[4-(SUBSTITUTED AMINO)-2-BUTYNL]BENZO[B]PYRROLO-[3,2,1-JK]-[1,4]BENZODIAZEPIN-6-ONES

[75] Inventors: Edward J. Glamkowski, Warren; Yulin Chiang, Convent Station, both of N.J.

[73] Assignee: Hoechst Marion Roussel Inc., Somerville, N.J.

[21] Appl. No.: 155,334

[22] Filed: Nov. 22, 1993

[51] Int. Cl.$^6$ ............ C07D 487/06; C07D 209/06; A61K 31/55

[52] U.S. Cl. ............ 514/219; 540/494

[58] Field of Search ............ 540/494; 514/219

[56] References Cited

U.S. PATENT DOCUMENTS

| | | | |
|---|---|---|---|
| 4,723,003 | 2/1988 | Glamkowski | 544/494 |
| 5,015,738 | 5/1991 | Glamkowski | 540/494 |

OTHER PUBLICATIONS

Ong, J. Med Chem. 24, 74(1981).
Geyer, J. Med Chem 25, 340(1982).
Ortmann Drug Devel. Design 4, 593–606 (1984).

*Primary Examiner*—Mark L. Berch
*Attorney, Agent, or Firm*—Barbara V. Maurer

[57] ABSTRACT

There are disclosed various compounds of the formula below,

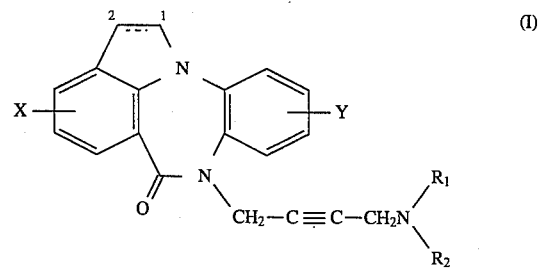

where the parameters X, Y, $R_1$ and $R_2$ are as defined in the specification which are useful as antidepressant and analgesic agents.

18 Claims, No Drawings

7-[4-(SUBSTITUTED AMINO)-2-BUTYNL]BENZO[B]PYRROLO-[3,2,1-JK]-[1,4]BENZODIAZEPIN-6-ONES

The present invention relates to compounds having Formula I depicted below,

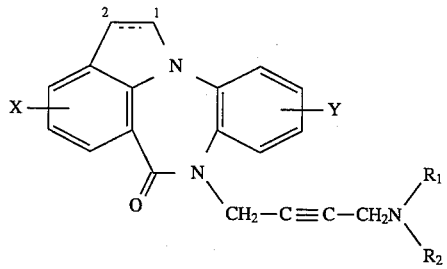

where,

X is hydrogen, halogen, loweralkyl, loweralkoxy or hydroxy;

Y is hydrogen, halogen, loweralkyl, loweralkoxy or hydroxy; and $R_1$ and $R_2$ are independently hydrogen or loweralkyl, or alternatively the group

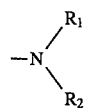

as a whole represents

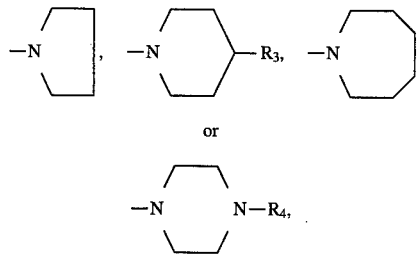

or

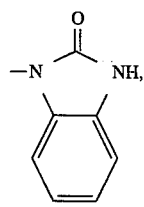

where $R_3$ is hydrogen, loweralkyl or

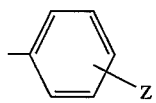

and $R_4$ is hydrogen, loweralkyl or

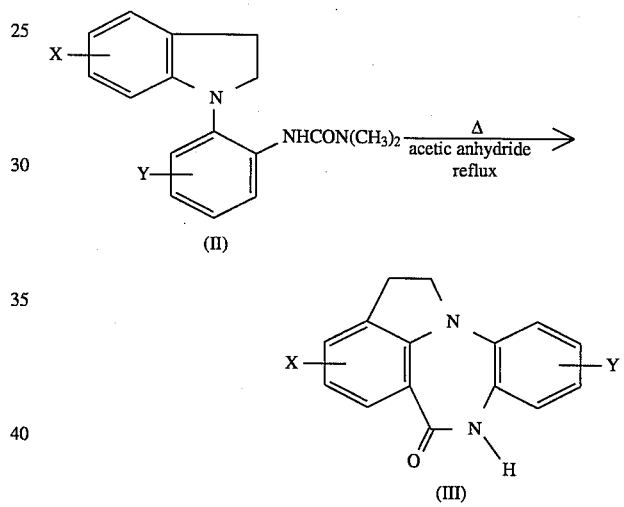

wherein Z is hydrogen, loweralkyl, loweralkoxy or halogen; and pharmaceutically acceptable acid addition salts thereof, which are useful as antidepressant and analgesic agents.

The dotted line present in Formula I and other structural formulas used in this invention means an optional double bond.

Unless otherwise stated or indicated, the following definitions shall apply throughout the specification and the appended claims.

The term loweralkyl shall mean a straight or branched alkyl group having from 1 to 6 carbon atoms. Examples of said loweralkyl include methyl, ethyl, n-propyl, isopropyl, n-butyl, iso-butyl, sec-butyl and straight- and branched-chain pentyl and hexyl.

The term halogen shall mean fluorine, chlorine, bromine or iodine.

Throughout the specification and the appended claims, a given chemical formula or name shall encompass all geometric, stereo, optical and tautomeric isomers where such isomers exist.

The compounds of this invention can be prepared by utilizing one or more of the synthetic steps described below.

Throughout the description of the synthetic steps, the notations X, Y, Z and $R_1$ through $R_4$ shall have the respective meanings given above unless otherwise stated or indicated.

STEP A:

A compound of Formula II is allowed to undergo a cyclization reaction to afford a compound for Formula III. Typically this cyclization reaction is conducted by heating compound II in a suitable solvent such as acetic anhydride under a reflux condition.

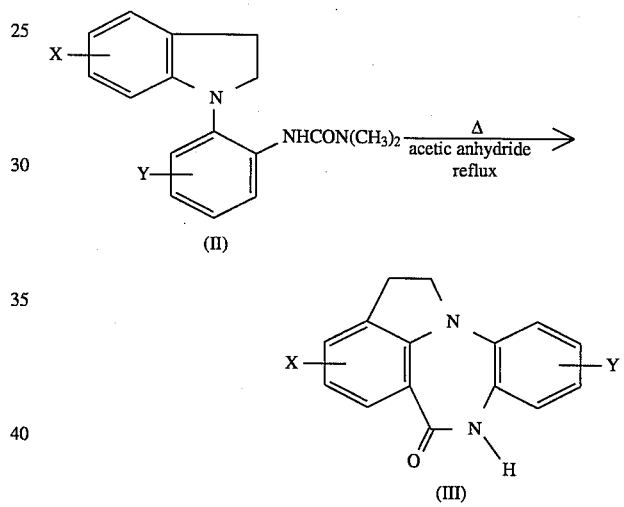

STEP B:

Compound III is allowed to react with 2,3-dichloro-5,6-dicyano-1,4-benzoquinone to undergo a dehydrogenation reaction to afford a compound of Formula IV. Typically this dehydrogenation reaction is conducted in a suitable solvent as xylene under a reflux condition.

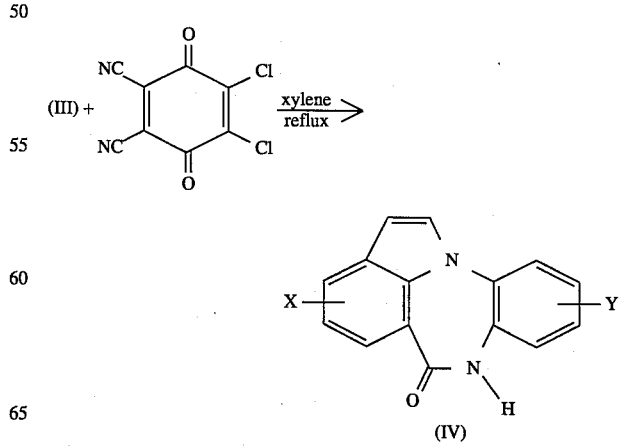

STEP C:

A compound of Formula V which is obtained either from STEP A or STEP B described above is allowed to react with a strong base such as sodium hydride to afford the corresponding anion. Typically, this reaction is conducted in a suitable medium such as dimethylformamide at room temperature. Subsequently, propargyl bromide is added to the reaction mixture and a substitution reaction depicted below is allowed to proceed in a suitable solvent such as toluene at ice temperature to afford a compound of Formula VI.

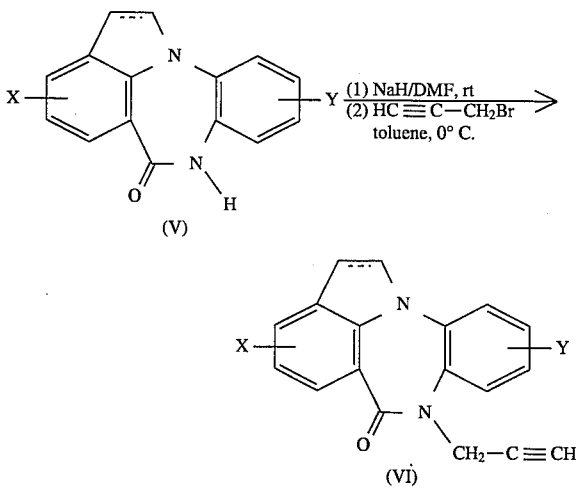

STEP D:

Compound VI is allowed to react with paraformaldehyde and an amine of Formula VII to afford a compound of Formula I. This reaction is typically conducted with the aid of cuprous chloride in a suitable solvent such as dioxane at room temperature.

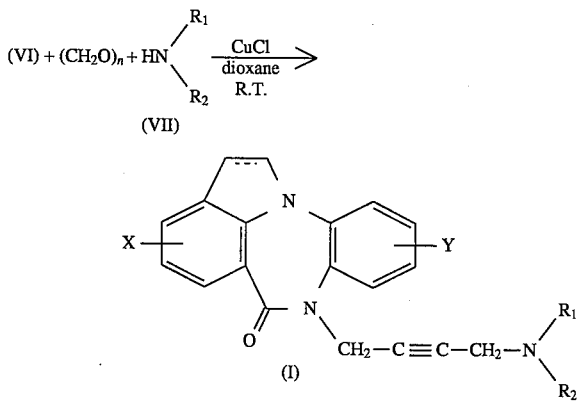

The compounds of Formula I of the present invention are useful for the treatment of depression. This utility is demonstrated by the activities of these compounds to enhance the central serotonergic function. Said activities are ascertained according to the protocol described below.

L-5-HYDROXYTRYPTOPHAN POTENTIATION IN RATS

Purpose:

According to the monoamine hypothesis of depression, compounds exert antidepressant activity because they are capable of enhancing central noradrenergic and/or serotonergic function (Shtee and Saarnivaara 1971; Douglas 1975; Lingjaerde 1973). This procedure is used to evaluate enhanced activity of the serotonergic system.

Method:

Groups of six male Wistar rats (150–200 g) are used in this test procedure. Four hours prior to 5-HTP (L-5-hydroxytryptophan) administration, pargyline HCl is prepared and administered by s.c. injection at 75 mg/kg in 1% saline and at a dosage volume of 1.0 ml/kg. Thirty minutes before the 5-HTP administration, drugs are prepared and dosed using distilled water and, if insoluble, a suitable surfactant is added. Control groups receive vehicle. Drugs are routinely administered i.p. at a dosage volume of 10 ml/kg.

L-5-hydroxytrpytophan (Calbiochem-Behring Corp.) is prepared at 1.0 mg/kg in distilled water and is administered i.p. in volumes proportional to 10 ml/kg. Fifteen minutes post-5-HTP treatment, each animal is observed for 10 seconds. Animal observations and 5-HTP administration are done in the presence of "white noise". In a dose range, drugs are administered in a randomized manner.

A compound is considered to potentiate 5-HTP activity if the animals exhibit continuous forelimb clonus. Potentiation is expressed as normalized percent potentiation relative to vehicle control. When a compound is observed to potentiate 5-HTP activity, a dose range using 10 animals/group is run in the same manner. An ED50 and 95% confidence limit are determined by Litchfield and Wilcoxon.

References:

Douglas, W. W.: Histamine and antihistamines: 5-Hydroxytryptamine and antagonists. In: The Pharmacological Basis of Therapeutics (Goodman, L. S. and Gilman, A., eds.), MacMillan Publishing Co., Inc., New York, 1975, pp. 613–629.

Lingjaerde Jr., O.: Effect of benzodiazepines on uptake and efflux of serotonin in human blood platelets in vitro. In: The Benzodiazepines (Garattini, S., Mussini, E. and Randall, L. O., eds.), Raven Press, New York, 1973, pp. 225–233.

Shtee, L. and Saamivaara, L.: The effect of drugs upon the uptake of 5-hydroxytryptamine and metraminol by human platelets. J. Pharm Pharmacol 23: 495–501, 1971.

Sigg, E. B.: Pharmacological studies with Tofranil. Can. Psychiatr. Assoc. J 4 (suppl): 75–85, 1959.

Results of the above test protocol for some of the compounds of this invention are presented in Table 1 along with a result for a reference compound.

TABLE 1

| Compound | $ED_{50}$(mg/kg, i.p.) or % Potentiation |
|---|---|
| 1,2-dihydro-7-[4-(4-methyl-1-piperidinyl)-2-butynyl]benzo[b]pyrrolo[3,2,1-jk][1,4]benzodiazepin-6-one hemifumarate | 25.3 mg/kg |
| 9-bromo-1,2-dihydro-7-[4-(4-methyl-1-piperazinyl)-2-butynyl]benzo[b]pyrrolo[3,2,1-jk][1,4]benzodiazepin-6-one fumarate | 50% @ 20 mg/kg |
| 9-bromo-1,2-dihydro-7-[4-[4-(2-methoxyphenyl)-1-piperazinyl]-2-butynyl]benzo[b]pyrrolo[3,2,1-jk][1,4]benzodiazepin-6-one | 50% @ 20 mg/kg |
| (Reference compound): Amitriptyline | 7.1 mg/kg |

The compounds of Formula I of the present invention are also useful as analgesic agents due to their ability to alleviate pain in mammals. The activity of the compounds is demonstrated in the 2-phenyl-1,4-benzoquinone-induced writhing test in mice, a standard assay for analgesia (Proc. Soc. Exptl. Biol. Med., 95,729 (1957). Table 2 shows results of the test for some of the compounds of this invention along with a result for a reference compound. The tests were conducted at the subcutaneous dose of 20 mg/kg.

TABLE 2

| Compound | Inhibition at 20 mg/kg, s.c. |
| --- | --- |
| 9-bromo-1,2-dihydro-7-[4-(4-methyl-1-piperidinyl)-2-butynyl]benzo[b]pyrrolo[3,2,1-jk][1,4]benzodiazepin-6-one hemifumarate | 41% |
| 1,2-dihydro-7-[4-(4-methyl-1-piperazinyl)-2-butynyl]benzo[b]pyrrolo[3,2,1-jk][1,4]benzodiazepin-6-one fumarate | 44% |
| 9-bromo-1,2-dihydro-7-[4-[4-(2-oxo-1H-benzimidazol-3-yl)-1-piperidinyl]-2-butynyl]benzo[b]pyrrolo[3,2,1-jk][1,4]benzodiazepin-6-one monohydrate | 42% |
| (Reference compound): Propoxyphene | $ED_{50} = 3.9$ mg/kg, s.c. |

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweeting agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds according to this invention include:
1,2-dihydro-7-(4-dimethylamino-2-butynyl)benzo[b]pyrrolo[3,2,1-jk][1,4]benzodiazepin-6-one;
1,2-dihydro-7-(4-diethylamino-2-butynyl)benzo[b]pyrrolo[3,2,1-jk][1,4]benzodiazepin-6-one;
1,2-dihydro-7-[4-(1-pyrrolidinyl)-2-butynyl]benzo[b]pyrrolo[3,2,1-jk][1,4]benzodiazepin-6-one;
1,2-dihydro-7-[4-(4-methyl-1-piperidinyl)-2-butynyl]benzo[b]pyrrolo[3,2,1-jk][1,4]benzodiazepin-6-one;
7-[4-(4-methyl-1-piperidinyl)-2-butynyl]benzo[b]pyrrolo[3,2,1-jk][1,4]benzodiazepin-6-one;
1,2-dihydro-7-[4-(4-methyl-1-piperidinyl)-2-butynyl]benzo[b]pyrrolo[3,2,1-jk][1,4]benzodiazepin-6-one;
9-bromo-1,2-dihydro-7-(4-dimethylamino-2-butynyl)benzo[b]pyrrolo[3,2,1-jk][1,4]benzodiazepin-6-one;
9-bromo-1,2-dihydro-7-[4-(1-pyrrolidinyl)-2-butynyl]benzo[b]pyrrolo[3,2,1-jk][1,4]benzodiazepin-6-one;
9-bromo-1,2-dihydro-7-[4-(4-methyl-1-piperidinyl)-2-butynyl]benzo[b]pyrrolo[3,2,1-jk][1,4]benzodiazepin-6-one;
9-bromo-1,2-dihydro-7-[4-(4-methyl-1-piperazinyl)-2butynyl]benzo[b]pyrrolo[3,2,1-jk][1,4]benzodiazepin-6-one;
9-bromo-7-[4-(4-methyl-1-piperazinyl)-2butynyl]benzo[b]pyrrolo[3,2,1-jk][1,4]benzodiazepin-6-one
9-bromo-1,2-dihydro-7-[4-[4-(2-methoxyphenyl)-1-piperazinyl]benzo[b]pyrrolo[3,2,1-jk][1,4]benzodiazepin-6-one; and
9-bromo-1,2-dihydro-7-[4-[4-(2-oxo-1H-benzimidazol-3-yl)-1-piperidinyl]-2-butynyl]benzo[b]pyrrolo[3,2,1-jk][1,4]benzodiazepin-6-one.

The following examples are presented in order to illustrate the present invention.

EXAMPLE 1

N-[2-(indolin-1-yl)phenyl]-dimethylaminocarboxamide

To a mixture of N-(2-aminophenyl)indoline (50.2 gm, 0.238 moles), sodium bicarbonate (42 gm, 2 eq) in butanone (190 ml) was added phenyl chloroformate (43 gm, 1.15 eq) dropwise at room temperature under $N_2$. The reaction was complete in 20 minutes. The mixture was cooled to 0° C. with an ice bath. Dimethylamine (gas) was bubbled through with vigorous stirring for 40 minutes. The progress of the reaction was followed with TLC till the spot for the phenyl carbamate intermediate had disappeared and was replaced by a lower $R_f$ spot of the desired product urea. The mixture was filtered, and the solvent was stripped. The crude oil was dissolved into dichloromethane (650 ml) and washed with 2N NaOH (2×250 ml), water and brine. The organic solution was dried over $MgSO_4$ and concentrated back to an oil. Purification was accomplished by flash chromatography on a silica gel column. The oil thus obtained was crystallized from ether (250 ml): weight 44 gm (66%), mp 76°–78° C.
Analysis:
Calculated for $C_{17}H_{19}N_3O$: 72.57%C 6.81%H 14.94%N
Found: 72.38%C 6.72%H 15.07%N

EXAMPLE 2

1,2-Dihydrobenzo[b]pyrrolo[3,2,1-jk][1,4]benzo-diazepin-6-one

N-[2-(Indolin-1-yl)phenyl]-dimethylaminocarboxamide (37 gm; 0.13 moles) in acetic anhydride (140 ml) was refluxed for 30 minutes. The mixture was cooled to ~50° C., and thereafter concentrated on a rotary evaporator to about 80 ml while crystallization occurred. The red solid was filtered and washed with ether. Recrystallization from chloroform (500 ml) afforded red-orange crystals: 21.3 gm (68%), m.p. 213.5°–214.5° C.
Analysis:
Calculated for $C_{15}H_{12}N_2O$: 76.25%C 5.12%H 11.86%N
Found: 76.03%C 5.14%H 11.92%N

EXAMPLE 3

Benzo[b]pyrrolo[3,2,1-jk][1,4]benzodiazepin-6-one 1,2-Dihydrobenzo[b]pyrrolo[3,2,1-jk][1,4]benzodiazepin-6-one (11.7 gm, 49.6 mmole) was heated in xylene (900 ml) to make a solution. To this 2,3-dichloro-5,6-dicyano-1,4-benzoquinone (DDQ, 12.2 gm, 1.08 eq) was added in one portion. The mixture was refluxed for 1 hour, then was allowed to cool to about 100° C. The mixture was filtered through a pad of celite. The solution was concentrated under reduced pressure (70° C., water bath) to about 600 ml. The solution was cooled to room temperature and the product crystallized out (7.99 gm; 69%).

Recrystallization from hot ethanol (900 ml) gave 4.62 gm of yellow needles, m.p. 226°–228° C.
Analysis:
Calculated for $C_{15}H_{10}N_2O$: 76.90%C 4.30%H 11.96%N
Found: 76.70%C 4.40%H 11.91%N

EXAMPLE 4

1,2-Dihydro-7-(2-propynyl)benzo[b]pyrrolo[3,2,1-jk]-[1,4]benzodiazepin-6-one A mixture prepared from 1,2-dihydrobenzo[b]pyrrolo[3,2,1-jk][1,4]-benzodiazepin-6-one (8.3 gm, 35 mmole) and sodium hydride (1.65 gm, 50% in oil, 1.0 eq) in dimethylformamide (DMF, 80 ml) was stirred at room temperature for 1.5 hours under $N_2$. It was cooled to ~0° C. To this solution was charged propargyl bromide (16.5 gm, 80% in toluene, 3 eq) and the mixture was stirred for another 1.5 hours at 0° C. At the end of the reaction, the solution was poured into 10% NaOH (250 ml), and extracted with dichloromethane (DCM 1 l). The DCM solution was washed with NaOH (250 ml), water (2×300 ml) and brine (2×300 ml), then dried over $MgSO_4$ and concentrated to an oil. Purification was accomplished by flash chromatography ($SiO_2$ column, 200 gm, eluted with 1:1 hexane:DCM, 4 l). The material thus purified weighed 7.1 gm, (74%) as an oil. It turned to solid upon trituration with ether. A 3 gram portion of this material was recrystallized from ether (150 ml) to afford 1.9 gm of yellow crystals, m.p. 104°–105° C.
Analysis:
Calculated for $C_{18}H_{14}N_2O$: 78.81%C 5.14%H 10.21%N
Found: 78.79%C 5.07%H 10.19%N

EXAMPLE 5

1,2,Dihydro-7-(4-dimethylamino-2-butynyl)-benzo[b]-pyrrolo[3,2,1-jk][1,4]benzodiazepin-6-one hemifumarate A mixture of 1,2-dihydro-7-(2-propynyl)-benzo[b]pyrrolo[3,2,1-jk][1,4]benzodiazepin-6-one (3.75 gm, 13.7 mmoles), paraformaldehyde (2.8 gm), dimethylamine (40% in $H_2O$, 4.11 gm, 2.0 eq) and copper (I) chloride (150 mg as catalyst) in dioxane (50 ml) was stirred for 3 hours at room temperature. After the reaction was complete, the mixture was diluted with dichloromethane (DCM, 150 ml). The insolubles were filtered through a pad of celite. The solution was concentrated on a rotary evaporator to an oil. The desired product was purified by flash chromatography over a silica gel column. The resultant oil (4.25 gm) was dissolved in ether (100 ml) and filtered once. The solution was added to a solution of fumaric acid in hot ethanol (25 ml) with fast stirring. The salt crashed out as a gum. This mixture was stirred for 1 hour while the gummy oil turned to solid. The solvents were removed, and the solid was recrystallized from hot ethanol (30 ml) to yield 3.58 gm, (67%), m.p. 161.5°–162.5° C.
Analysis:
Calculated for $C_{21}H_{21}N_3O \cdot 0.5\ C_4H_4O_4$: 70.93%C 5.95%H 10.79%N
Found: 70.99%C 6.08%H 10.80%N

EXAMPLE 6

1,2-Dihydro-7-(4-diethylamino-2-butynyl)benzo[b]-pyrrolo[3,2,1-jk][1,4]benzo-diazepin-6-one hemifumarate A mixture of 1,2-dihydro-7-(2-propynyl)-benzo[b]pyrrolo[3,2,1-jk][1,4]benzodiazepin-6-one (4.0 gm, 18.24 mmoles), paraformaldehyde (3.2 gm), diethylamine (2.67 gin, 2 eq) and copper (I) chloride (150 mg) in dioxane (50 ml) was stirred at room temperature for 0.5 hour. The mixture was diluted with dichloromethane (150 ml). The insolubles were filtered through a pad of celite. The solution was concentrated to an oil. The desired product was purified by flash chromatography over a silica gel (100 gm, eluted with 1% $CH_3OH$:1% diethylamine:98% DCM, 2 l). The resultant oil (5.9 gm), was dissolved into ether (150 ml) and filtered once, then added into a solution of fumaric acid (2.53 gm, 1.2 eq) in ethanol (35 ml). The mixture was stirred for 3 hours until all the oily precipitates turned to a solid. The solid was collected and recrystallized twice from hot ethanol (100 ml) to yield 4.35 gm, 57%, m.p. 159°–160° C.

Analysis:
  Calculated for $C_{23}H_{25}N_3O \cdot 0.5\ C_4H_4O_4$: 71.92%C 6.52%H 10.06%N
  Found: 71.73%C 6.60%H 10.17%N

EXAMPLE 7

1,2-Dihydro-7-[4-(1-pyrrolidinyl)-2-butynyl]benzo[b]pyrrolo[3,2,1jk][1,4]benzodiazepin-6-one A mixture of 1,2-dihydro-7-(2-propynyl)-benzo[b]pyrrolo[3,2,1-jk][1,4]benzodiazepin-6-one (3.0 gm, 10.9 mmoles), paraformaldehyde (2.4 gm), pyrrolidine (780 mg, 1.1 eq), copper(I) chloride (150 mg) in dioxane (50 ml) was stirred for 16 hours at room temperature. After the reaction was complete, the mixture was diluted with dichloromethane (250 ml). The insolubles were filtered through a pad of celite. The solution was concentrated to an oil. The desired product was purified by flash chromatography over a silica gel column ($SiO_2$, 100 gm; eluted with 1:1:98, methanol:dimethylamine:DCM; 1.5 l) to afford a light yellow syrup (4.3 gm). This oil turned to a solid upon trituration with ether. This material was recrystallized from ether (40 ml) at 0° C. Yield:2.3 gm (59%), m.p. 80°–81° C.
Analysis:
  Calculated for $C_{23}H_{23}N_3O$: 77.28%C 6.49%H 11.76%N
  Found: 77.41%C 6.56%H 11.80%N

EXAMPLE 8

1,2-Dihydro-7-[4-(4-methyl-1-piperidinyl)-2-butynyl]-benzo[b]pyrrolo[3,2,1-jk][1,4]benzodiazepin-6-one hemifumarate A mixture of 1,2-dihydro-7-(2-propynyl)-benzo[b]pyrrolo[3,2,1-jk][1,4]benzodiazepin-6-one (4.45 gm, 16.2 mmole), paraformaldehyde (3.6 gm), 4-methylpiperidine (1.93 gm, 1.2 eq) and copper(I) chloride (300 mg), in dioxane (75 ml) was stirred for 16 hours at room temperature. After the reaction was complete, the mixture was diluted with dichloromethane (DCM, 300 ml). The insolubles were filtered off through a pad of celite. The solution was concentrated on a rotary evaporator to an oil (48 gm). The desired product was purified by flash chromatography over a silica gel column (100 gm, $SiO_2$, eluted with 1% $CH_3OH$:1% diethylamine:98% DCM, 1.5 l). The material obtained as a yellow syrup was dissolved in ether (50 ml) and filtered once. The ethereal solution was added to a solution of fumaric acid (1.9 gm, 1.0 eq) in ether (30 ml) with fast stirring. The salt crashed out as a thick gum. This mixture was diluted with ether (300 ml) and stirred for i hour, while the gum turned slowly to a solid. The solid was collected and recrystallized once from hot ethanol to afford yellow crystals: 3.9 gm, m.p. 157°–158° C.
Analysis:
  Calculated for $C_{25}H_{27}N_3O \cdot 0.5\ C_4H_4O_4$: 73.11%C 6.59%H 9.47%N
  Found: 72.82%C 6.84%H 9.24%N

EXAMPLE 9

1,2-Dihydro-7-[4-(4-methyl-1-piperazinyl)-2-butynyl]-benzo[b]pyrrolo[3,2,1-jk][1,4]benzodiazepin-6-one fumarate A mixture of 1,2-dihydro-7-(2-propynyl)-benzo[b]pyrrolo[3,2,1-jk][1,4]benzodiazepin-6-one (4 gm, 14.6 mmoles), N-methylpiperazine (2.92 gm, 2 eq), paraformaldehyde (3.2 gm), and copper(I) chloride (300 mg) in dioxane (50 ml) was stirred for 24 hours at room temperature. The mixture was diluted with dichloromethane (350 ml). The insolubles were filtered through a pad of celite. The solution was concentrated on a rotary evaporator to an oil (~9 gm). The desired product was purified by flash chromatography over a silica gel column (125 gm, eluted with DCM, 300 ml; 1% $CH_3OH$:1% diethylamine:98% DCM, 1.3 l). The pure material obtained as a yellow oil (3.4 gm, 60%) was dissolved in ether (100 ml) and filtered once. The ether solution was added to a solution of fumaric acid (1.2 gm, 1.1 eq) in hot ethanol (30 ml) with fast stirring. The salt crashed out as a thick oil. This mixture was stirred for 1.5 hours while the oil turned to a solid. The solid was collected. Recrystallization from hot ethanol gave yellow crystals: 3.4 gm (46%), m.p. 186.5°–187.5° C.
Analysis:
  Calculated for $C_{24}H_{26}N_4O \cdot C_4H_4O_4$: 66.91%C 6.02%H 11.15%N
  Found: 66.73%C 6.09%H 11.24%N

EXAMPLE 10

9-Bromo-1,2-dihydro-7-(2-propynyl)benzo[b]pyrrolo-[3,2,1-jk][1,4]benzodiazepin-6-one A solution of 9-bromo-1,2-dihydrobenzo[b]pyrrolo[3,2,1-jk][1,4]benzodiazepin-6-one (8.0 gm, 25.4 mmoles) in dimethylformamide (DMF, 120 ml) was stirred with sodium hydride (50% oil suspension, 1.9 gm, 1.6 eq) at ~0° C. (water bath) for 1.5 hours. Propargyl bromide (80% wt in toluene, 7.5 gm, 2 eq) was charged in one portion. The mixture was stirred for 30 minutes. After the starting material was consumed (TLC, dichloromethane), the solution was diluted with dichloromethane, then washed with water (3×500 ml) and brine (2×500 ml). The solution was dried over $MgSO_4$, and concentrated on a rotary evaporator to an oil.

Purification was effected by flash chromatography over a silica gel column (150 gm, eluted with DCM, 2). The material thus obtained with triturated with ether to a solid (8.7 gm). Recrystallization from isopropylether (150 ml) yielded yellow crystals: 6.16 gm, m.p. 150°–151° C.
Analysis:
  Calculated for $C_{18}H_{13}N_2BrO$: 61.20%C 3.71%H 7.93%N
  Found: 61.26%C 3.81%H 7.79%N

EXAMPLE 11

9-Bromo-1,2-dihydro-7-(4-dimethylamino-2-butynyl)-benzo[b]pyrrolo[3,2,1-jk][1,4]benzodiazepin-6-one hemifumarate A mixture of 9-bromo-1,2-dihydro-7-(2-propynyl)-benzo[b]pyrrolo[3,2,1-jk][1,4]benzodiazepin-6-one (4.0 gm, 11.3 mmoles), paraformaldehyde (3 gm), dimethylamine (40% in water, 4 gm, 3 eq) and CuCl (150 mg) in 1,4-dioxane (50 ml) was stirred at room temperature for 30 minutes, then heated on a water bath (50° C.) for 2 hours. When the reaction was over, the mixture was diluted with dichloromethane (200 ml). The insolubles were filtered through a pad of celite. The solution was concentrated to a crude oil (7.5 gm). The desired product was purified by flash chromatography on a silica gel column ($SiO_2$, 65 gm, eluted with 1% $CH_3OH$:0.5% diethylamine:99% DCM, 1.2 l). The material thus obtained weighed 4.58 gm (98%). This oily product was dissolved in ether and added to a solution of fumaric acid (1.27 gm, 1.0 eq) in hot ethanol (15 ml). Crystals (4.75 gm) were formed slowly over a 2 hour period. Recrystallization from hot acetone (350 ml, concentrated down to 75 ml) yielded 4.21 gm, 71%, of light yellow crystals, top: 177°–179° C.
Analysis:
Calculated for $C_{21}H_{20}BrN_3O \cdot 0.5\ C_4H_4O_4$: 58.90%C 4.73%H 8.97%N
Found: 58.64%C 4.80%H 8.73%N

EXAMPLE 12

9-Bromo-1,2-dihydro-7-[4-(1-pyrrolidinyl)-2-butynyl]benzo[b]-pyrrolo[3,2,1-jk][1,4]-benzodiazepin-6-one A mixture of 9-bromol-1,2-dihydro-7-(2-propynyl)-benzo[b]pyrrolo[3,2,1-jk][1,4]benzodiazepin-6-one (2.0 gm, 5.66 mmoles), paraformaldehyde (1.2 gm), pyrrolidine (380 mg), copper(I) chloride (0.1 gm) in 1,4-dioxane (40 ml) was stirred for 1 hour at 45° C. The mixture was diluted with dichloromethane (150 ml), then filtered through celite. The solution was concentrated to an oil (3.2 gm). This was purified further by flash chromatography over silica gel (30 gm SiO$_2$, eluted with 1.5% CH$_3$OH: DCM, 1 l). Recrystallization of the purified material from ether (100 ml) afforded 2.12 gm, m.p. 121°–122.5° C. (86% overall yield).
Analysis:
Calculated for
$C_{23}H_{22}N_3BrO$: 63.31%C 5.08%H 9.63%N
Found: 63.02%C 5.11%H 9.55%N

EXAMPLE 13

9-Bromo-1,2-dihydro-7-[4-(4-methyl-1-piperidinyl)-2-butynyl]benzo[b]pyrrolo[3,2,1-jk][1,4]benzodiazepin-6-one hemifumarate A mixture of 9-bromo- 1,2-dihydro-7-(2-propynyl)-benzo[b]pyrrolo[3,2,1-jk][1,4]benzodiazepin-6-one (5.3 gm, 15 mmoles), paraformaldehyde (3.6 gm), 4-methylpiperazine (1.85 gm, 1.2 eq) and copper(I) chloride (300 mg) in dioxane (75 ml) was stirred for 16 hours at room temperature. The mixture was diluted with dichloromethane (300 ml). The insolubles were filtered through a pad of celite. The solution was concentrated on a rotary evaporator to an oil which was purified by flash chromatography over a silica gel column (125 gm, eluted with DCM, 1 l, 1% CH$_3$OH:1% diethylamine:98% DCM, 1.2 l). The material (5.6 gm, 80%) obtained as an oil was dissolved in ether (300 ml) and filtered once. The ether solution was added to a solution of fumaric acid (1.5 gm, 1.1 eq) in ethanol (30 ml) with fast stirring. The salt crashed out as a thick gum. This mixture was stirred for 2 hours, while the gummy oil turned to a powdery solid. The solid was collected. Recrystallization from ethanol gave yellow crystals: 2.63 gm, m.p. 154°–155° C.
Analysis:
Calculated for $C_{25}H_{26}BrN_3O \cdot 0.5\ C_4H_4O_4$: 62.07%C 5.40%H 8.04%N
Found: 61.90%C 5.49%H 7.93%N

EXAMPLE 14

9-Bromo-1,2-dihydro-7-[4-(4-methyl-1-piperazinyl)-2-butynyl]benzo[b]pyrrolo[3,2,1-jk][1,4]benzodiazepin-6-one fumarate A mixture of 9-bromo-1,2-dihydro-7-(2-propynyl)-benzo[b]pyrrolo[3,2,1-jk][1,4]benzodiazepin-6-one (3.47 gm, 9.8 mmoles), paraformaldehyde (1.2 gm), N-methylpiperazine (3.0 gm, 3 eq), copper(I) chloride (300 mg) in dioxane (50 ml) was heated for 1.5 hours at reflux. After the reaction, the mixture was diluted with dichloromethane (200 ml). The insolubles were filtered through a pad of celite. The solution was concentrated to an oil (7.4 gm). Purification was effected by flash chromatography on a silica gel column (70 gm, eluted with 1% CH$_3$OH: 1% diethylamine:98% DCM, 1.5 l). The material, obtained as an oil (3.0 gm, 58%), was dissolved into ether and filtered once. The ether solution (~30 ml) was added to a solution of fumaric acid (0.8 gm, 1.05 eq) in ethanol. The product salt crystallized out slowly, 2.52 gm. Recrystallization from hot ethanol (75 ml) yielded yellow crystals: 2.1 gm, m.p. 112°–114° C.
Analysis:
Calculated for $C_{24}H_{25}BrN_4O \cdot C_4H_4O_4$: 57.83%C 5.03%H 9.64%N
Found: 57.86%C 5.24%H 9.89%N

EXAMPLE 15

9-Bromo-1,2-dihydro-7-[4-[4-(2-methoxyphenyl)-1-piperazinyl]-2-butynyl]-2-butynyl]benzo[b]pyrrolo-[3,2,1-jk][1,4]benzodiazepin-6-one A mixture of 9-bromo-1,2-dihydro-7-(2-propynyl)-benzo[b]pyrrolo[3,2,1-jk][1,4]benzodiazepin-6-one (4.0 gm, 11.3 mmoles), paraformaldehyde (2.9 gm), 1-(2-methoxyphenyl)-piperazine (4.38 gm, 2 eq), and copper(I) chloride (200 mg) in doxane (50 ml) was stirred at room temperature for 3 hours. The reaction was monitored by TLC on silica plates. At the end of the reaction, the mixture was diluted with dichloromethane, then filtered through a pad of celite. The solution was concentrated to an oil. The purification was effected by flash chromatography twice on silica gel [(1) 180 gm SiO$_2$; eluted with 2% CH$_3$OH:98% DCM, 1.5 l; (2) 100 gm SiO$_2$, eluted with DCM, 2 l, 1% CH$_3$OH:DCM, 2 l]. The product thus obtained was concentrated to an oil which crystallized from ether, weight: 3.0 gm, m.p. 188°–189° C., the second crop yielded 2.09 gm, the total being 5.09 gm (83%).
Analysis:
Calculated for $C_{30}H_{29}BrN_4O_2$: 64.63%C 5.24%H 10.05%N
Found: 64.55%C 5.22%H 9.81%N

EXAMPLE 16

9-Bromo-1,2-dihydro-7-[4-[4-(2-oxo-1H-benzimidazol-3-yl)-1-piperidinyl-2-butynyl]benzo[b]pyrrolo-[3,2,1-jk][1,4]benzodiazepin-6-one monohydrate A mixture of 9-bromo- 1,2-dihydro-7-(2-propynyl)-benzodiazepin-6-one (4.0 gm, 11.32 mmoles), paraformaldehyde (3.0 gm), 4-(2-oxo-1H-benzimidazol-3-yl)piperidine (3.69 gm, 1.5 eq) and CuCl (300 mg) in dioxane (50 ml) was stirred at room temperature overnight. The crude mixture was filtered and concentrated to an oil (10.5 gm). Purification was effected by flash chromatography (SiO$_2$, 100 gm, eluted with dichloromethane (DCM) 1 l, 1% CH$_3$OH:DCM, 2 l). The material thus purified weighed 3.78 gm as a yellow solid. Recrystallization from chloroform (40 ml) and ether (30 ml) yielded 3.16 gm of yellow crystals, mp 247°–249° C.
Analysis:
Calculated for $C_{31}H_{28}BrN_5O_2 \cdot H_2O$: 62.00%C 5.03%H 11.66%N
Found 61.87%C 4.68%H 11.39%N

We claim:
1. A compound of the formula

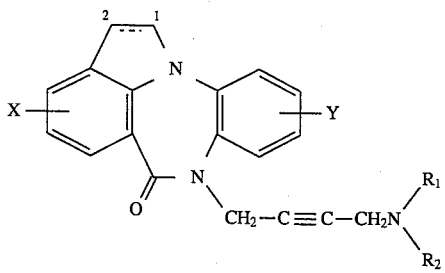

where,

X is hydrogen, halogen, loweralkyl, loweralkoxy or hydroxy;

Y is hydrogen, halogen, loweralkyl, loweralkoxy or hydroxy; and $R_1$ and $R_2$ are independently hydrogen or loweralkyl, or alternatively the group

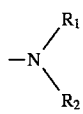

as a whole represents

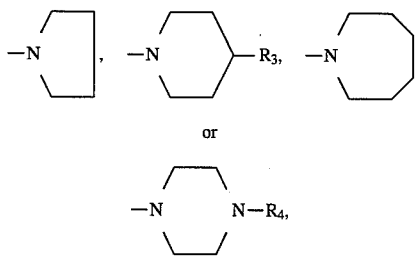

where $R_3$ is hydrogen, loweralkyl or

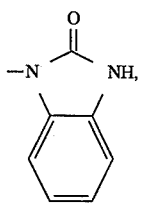

and $R_4$ is hydrogen, loweralkyl or

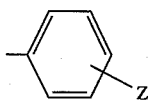

wherein Z is hydrogen, loweralkyl, loweralkoxy or halogen; or a pharmaceutically acceptable acid addition salts thereof.

2. The compound as defined in claim 1, where X is hydrogen.

3. The compound as defined in claim 1, where Y is hydrogen or halogen.

4. The compound as defined in claim 1, where X is hydrogen and Y is hydrogen or halogen.

5. The compound as defined in claim 1, where Y is bromine.

6. The compound as defined in claim 1, which is 1,2-dihydro-7-(4-dimethylamino-2-butynyl)-benzo[b]pyrrolo[3,2,1-jk][1,4]benzodiazepin-6-one.

7. The compound as defined in claim 1, which is 1,2-dihydro-7-(4-diethylamino-2-butynyl)benzo[b]pyrrolo[3,2,1-jk][1,4]benzodiazepin-6-one.

8. The compound as defined in claim 1, which is 1,2-dihydro-7-[4-(1-pyrrolidinyl)-2-butynyl]benzo[b]pyrrolo[3,2,1-jk][1,4]benzodiazepin- 6-one.

9. The compound as defined in claim 1, which is 1,2-dihydro-7-[4-(4-methyl-1-piperidinyl)-2-butynyl]benzo[b]pyrrolo[3,2,1-jk][1,4]-benzodiazepin- 6-one.

10. The compound as defined in claim 1, which is 1,2-dihydro-7-[4-(4-methyl-1-piperazinyl)-2-butynyl]benzo[b]pyrrolo[3,2,1-jk][1,4]-benzodiazepin- 6-one.

11. The compound as defined in claim 1, which is 9-bromo-1,2-dihydro-7-(4-dimethylamino-2-butynyl)-benzo[b]pyrrolo[3,2,1-jk][1,4]-benzodiazepin- 6-one.

12. The compound as defined in claim 1, which is 9-bromo-1,2-dihydro-7-[4-(1-pyrrolidinyl)-2-butynyl]benzo[b]pyrrolo[3,2,1-jk][1,4]-benzodiazepin- 6-one.

13. The compound as defined in claim 1, which is 9-bromo-1,2-dihydro-7-[4-(4-methyl-1-piperidinyl)-2-butynyl]benzo[b]pyrrolo[3,2,1-jk][1,4]benzodiazepin-6-one.

14. The compound as defined in claim 1, which is 9-bromo-1,2-dihydro-7-[4-(4-methyl-1-piperazinyl)-2-butynyl]benzo[b]pyrrolo[3,2,1-jk][1,4]benzodiazepin-6-one.

15. The compound as defined in claim 1, which is 9-bromo-1,2-dihydro-7-[4-[4-(2-methoxyphenyl)-1-piperazinyl]-2-butynyl]benzo[b]pyrrolo[3,2,1-jk][1,4]benzodiazepin-6-one.

16. The compound as defined in claim 1, which is 9-bromo-1,2-dihydro-7-[4-[4-(2-oxo-1H-benzimidazol-3-yl)-1-piperidinyl]-2-butynyl]benzo[b]pyrrolo[3,2,1-jk][1,4]benzodiazepin-6-one.

17. A pharmaceutical composition comprising a compound as defined in claim 1 in an amount effective for alleviating pain and a suitable carrier therefor.

18. A method of treating a patient in need of relief from pain which comprises administering to the patient an effective amount of a compound as defined in claim 1.

* * * * *